(12) United States Patent
Fraser et al.

(10) Patent No.: US 9,078,991 B2
(45) Date of Patent: Jul. 14, 2015

(54) VASCULAR DILATOR SYSTEMS, KITS, AND METHODS

(71) Applicant: Vascular Solutions, Inc., Minneapolis, MN (US)

(72) Inventors: Doug Fraser, Wilmslow (GB); Howard Root, Excelsior, MN (US); Thomas Holman, Princeton, MN (US); Deepa Deepa, Minneapolis, MN (US)

(73) Assignee: Vascular Solutions, Inc., Minneapolis, MN (US)

( * ) Notice: Subject to any disclaimer, the term of this patent is extended or adjusted under 35 U.S.C. 154(b) by 200 days.

(21) Appl. No.: 13/784,073

(22) Filed: Mar. 4, 2013

(65) Prior Publication Data

US 2014/0249562 A1  Sep. 4, 2014

(51) Int. Cl.
*A61M 29/00* (2006.01)
*A61M 25/06* (2006.01)

(52) U.S. Cl.
CPC ....... *A61M 29/00* (2013.01); *A61M 2025/0681* (2013.01)

(58) Field of Classification Search
CPC ............... A61M 29/00; A61M 29/02; A61M 2025/0681; A61M 39/1011; A61M 2039/1033; A61M 2039/1038; A61M 2039/1083; A61M 2039/1088; A61B 2017/1205; A61B 2017/12054; A61B 2017/3433; A61B 2017/3435; A61B 2017/3447; A61B 2017/347; A61B 17/3417; A61B 17/3415; A61B 17/3431; A61B 17/3429; A61B 17/320758; A61B 17/320725; A61F 2/958

See application file for complete search history.

(56) References Cited

U.S. PATENT DOCUMENTS

| | | | | |
|---|---|---|---|---|
| 5,385,562 A | * | 1/1995 | Adams et al. | 604/528 |
| 5,389,090 A | * | 2/1995 | Fischell et al. | 604/528 |
| 6,135,991 A | * | 10/2000 | Muni et al. | 604/509 |
| 6,939,328 B2 | | 9/2005 | Raulerson | |
| 8,109,908 B1 | | 2/2012 | Kraus et al. | |
| 2009/0312786 A1 | * | 12/2009 | Trask et al. | 606/192 |
| 2012/0095432 A1 | | 4/2012 | Nath | |
| 2012/0095448 A1 | * | 4/2012 | Kajii | 604/528 |
| 2012/0179102 A1 | * | 7/2012 | Blanchard et al. | 604/164.1 |

* cited by examiner

*Primary Examiner* — Jocelin Tanner
(74) *Attorney, Agent, or Firm* — Schwegman, Lundberg & Woessner, P.A.

(57) ABSTRACT

Vascular dilator systems, kits, and methods allowing for sheathless introduction of a treatment device into a body vessel or body cavity are disclosed. A vascular dilator system can include a dilator assembly, including a tubular shaft and a deformable member, and optionally, the treatment device. The deformable member can include a non-biodegradable material and can have a diameter at a proximal end portion that is greater than a diameter at a distal end portion. The distal end portion of the deformable member can be coupled to an outer surface of the tubular shaft, at or near a shaft distal end portion. The proximal end portion of the deformable member can include a diameter configured to receive or stretch around a distal end portion of the treatment device. In use, the deformable member can provide a tapered bridge between the outer surface of the tubular shaft and an outer surface of the treatment device.

27 Claims, 7 Drawing Sheets

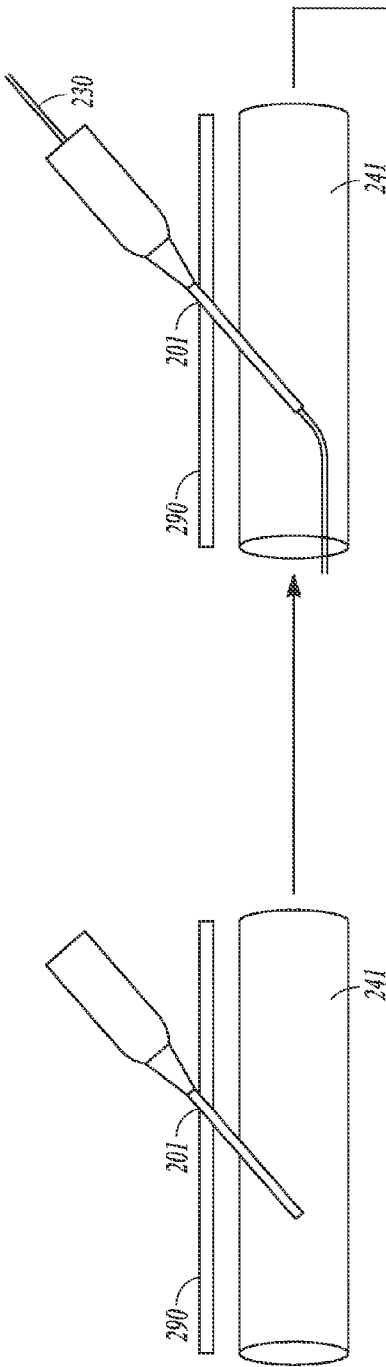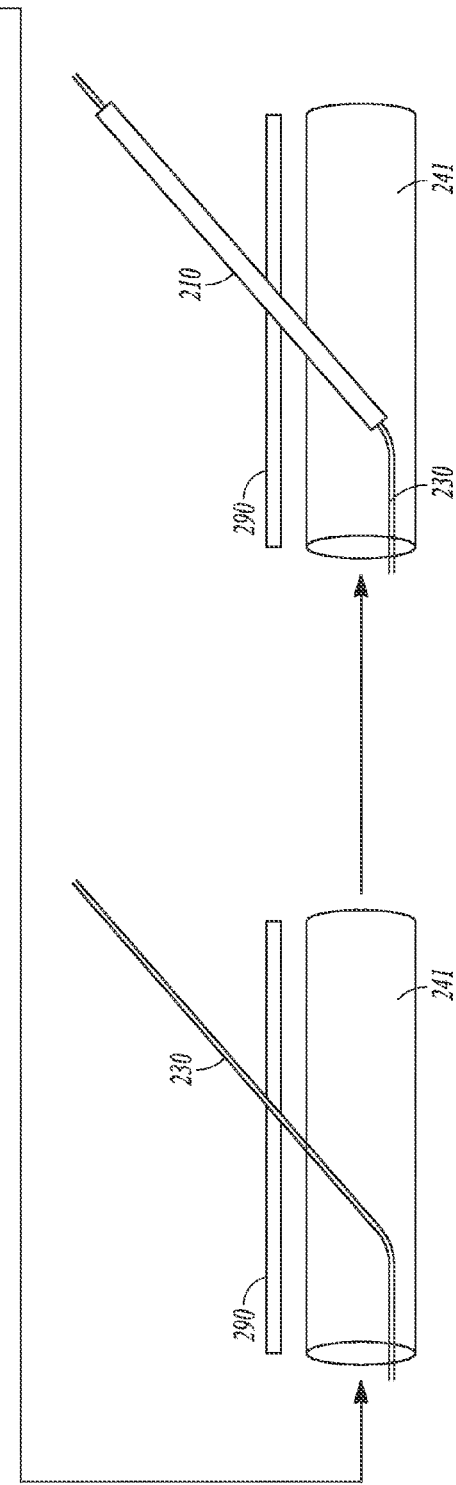

VASCULAR DILATOR SYSTEMS, KITS, AND METHODS

TECHNICAL FIELD

This patent document pertains generally to systems, kits, and methods to introduce a treatment device into a body vessel or body cavity. More particularly, but not by way of limitation, this patent document pertains to vascular dilator systems, kits, and methods configured to protect body vessel or body cavity wall surfaces, while preserving vessel or cavity access size.

BACKGROUND

Minimally invasive procedures have been implemented in a variety of medical settings, such as for vascular interventions, stenting, embolic protection, electrical heart stimulation, heart mapping and visualization, and the like. These procedures generally rely on accurately navigating and placing treatment devices within a body vessel or body cavity.

During minimally invasive procedures, a body vessel, for example, can be accessed through a small access hole. The small access hole can be initiated by piercing the skin, the body vessel, and any intermediate structures using a hollow needle (e.g., a trocar or a hypodermic needle). With the hollow needle in place, a guide wire can be advanced within an inner lumen of the needle and into the body vessel, thereby providing a "railway" to the vessel. Upon removing the hollow needle, such as by sliding it off a proximal end of the guide wire, one or more elongate treatment devices (e.g., guide catheters, diagnostic catheters, electrical leads, and other interventional devices) can be advanced over the guide wire and into the body vessel, such as for use in a diagnostic, therapeutic, or other procedure.

There are many risks involved with advancing treatment devices over a guide wire and into a body vessel or body cavity. For example, a distal end of a treatment device can skive or otherwise damage a wall of a body vessel, particularly as the device is introduced into the vessel or passes through narrow passages or tortuous vessel anatomy involving sharp bends. Advancement of treatment devices also risks dislodging embolic material or even perforating the vessel wall due to an open distal end edge of the treatment devices catching or "fish mouthing" on an opening or other irregularity of the wall.

OVERVIEW

To help minimize or prevent damage to a wall of a body vessel or body cavity during insertion of a treatment device, a fixed-diameter tubular introducer sheath is often used by caregivers to act as an intermediary between the treatment device and the body vessel or body cavity wall. However, conventional tubular introducer sheaths have relatively large cross-sectional sizes and, after establishing vessel or cavity access, are discarded. These large cross-sections occupy valuable access space and make it impossible to internally advance treatment devices having an outer diametrical size approximately equal to or greater than a natural inner diameter of a body vessel or body cavity. Accordingly, many minimally invasive procedures that would desirably be performed by a caregiver using a radial artery, for example, are rerouted to a larger femoral artery, which provides the necessary access space for a tubular introducer sheath and the desired treatment device. Similarly, other minimally invasive procedures that would desirably be performed by caregivers using a femoral artery are rerouted elsewhere.

The present inventors recognize that it can be desirable to provide caregivers with the ability to introduce treatment devices, such as guide, diagnostic, or therapeutic catheters, having an outer surface diameter approximately equal to, or in some cases greater than, the natural inner diameter of a body vessel or body cavity. At the same time, the present inventors recognize the importance of a system for introducing treatment devices in a safe manner, such as a system which inhibits tearing or damage of a body vessel or body cavity wall, patient discomfort, and/or involuntary vessel or cavity spasm as the treatment device is internally advanced.

Vascular dilator systems, kits, and methods allowing for sheathless introduction of a treatment device into a body vessel or body cavity in a safe and relatively pain free manner are disclosed. A vascular dilator system can include a dilator assembly, including a tubular shaft and a deformable member, and optionally, the treatment device or a portion of the treatment device. The vascular dilator system can position the treatment device at a desired location within the body vessel or body cavity, while preserving vessel or cavity access size.

The tubular shaft can be configured to be advanced over a guide wire and into the body vessel or body cavity. The tubular shaft can have an outer surface that increases in diameter between a shaft distal end portion and a shaft proximal end portion, thereby providing a gradual taper from a relatively small diameter of the guide wire to a larger diameter of the surrounding treatment device.

The deformable member can include a non-biodegradable material and can have an inner surface that increases in diameter between a distal end and a proximal end. A distal end portion of the deformable member can be coupled to the outer surface of the tubular shaft, at or near the shaft distal end portion. A proximal end portion of the deformable member can include an inner surface diameter configured to receive the outer surface at a distal end portion of the treatment device. In some examples, the inner surface of the deformable member's distal end and the inner surface of the deformable member's proximal surface are part of the same surface, such as when the deformable member is coupled to the outer surface of the tubular shaft so that the proximal end initially has a proximal-facing orientation to receive the distal end portion of the treatment device. In other examples, the inner surface of the deformable member's distal end and the inner surface of the deformable member's proximal end are on opposite surfaces, such as when the deformable member is coupled to the outer surface of the tubular shaft so that the proximal end initially has a distal-facing orientation and has to be inverted onto itself (i.e., overturned) before being coupled to the distal end portion of the treatment device. In use, the deformable elastic member can provide a smooth, edge free surface that provides a tapered bridge over a gap between the outer surface of the tubular shaft and the outer surface of the treatment device.

When the treatment device is positioned as desired within the body vessel or body cavity of interest, the dilator assembly can be retracted by pulling on the shaft proximal end portion. During retraction, distal end portions of the dilator assembly are slid through a lumen of the treatment device and, in the process, the proximal end portion of the deformable member can be inverted onto the reduced-diameter of the shaft distal end portion. The inverting of the proximal end portion of the deformable member onto the reduced-diameter portion of the tubular shaft allows the deformable member and the tubular shaft to fit through the lumen of the treatment device. The orientation of the proximal end of the deformable member, when its distal end is coupled to the tubular shaft, will determine whether one or two layers of the deformable member are positioned (on a per side basis) between the outer surface of the tubular shaft and lumen walls of the treatment device during retraction.

To better illustrate the vascular dilator systems and methods disclosed herein, a non-limiting list of examples is provided here:

In Example 1, a system can comprise a dilator assembly including a tubular shaft and a deformable member. The tubular shaft can have an outer surface increasing in diameter between a shaft distal end portion and a shaft proximal end portion. The deformable member can include a non-biodegradable material and can have an inner surface diameter at a deformable member proximal end portion, as positioned during advancement within a body vessel or body cavity, which is greater than an inner surface diameter at a deformable member distal end portion, as positioned during advancement within the body vessel or body cavity. The deformable member distal end portion can be coupled to the outer surface of the tubular shaft, at or near the shaft distal end portion.

In Example 2, the system of Example 1 can optionally further comprise one or more treatment devices. A treatment device can extend a length less than a length of the tubular shaft, from a device proximal end portion to a device distal end portion, and can have a lumen diameter greater than a largest diameter of the outer surface of the tubular shaft.

In Example 3, the system of Example 2 can be optionally configured such that the lumen diameter is sufficiently sized to allow the tubular shaft and the deformable member to be removed, from the device proximal end, through the treatment device lumen when the proximal end portion of the deformable member is folded back around the shaft distal end portion.

In Example 4, the system of any one or any combination of Examples 2 or 3 can be optionally configured such that the device distal end portion is received over the tubular shaft, at the shaft proximal end portion, and advanced to a location adjacent the deformable member proximal end portion.

In Example 5, the system of Example 4 can be optionally configured such that the inner surface diameter at the deformable member proximal end portion, as positioned during advancement within the body vessel or body cavity, receives and surrounds an outer surface of the treatment device at the device distal end portion.

In Example 6, the system of Example 5 can be optionally configured such that the inner surface diameter at the deformable member proximal end portion, as positioned during advancement within the body vessel or body cavity, is greater than an outer surface diameter of the treatment device at the device distal end portion.

In Example 7, the system of any one or any combination of Examples 5 or 6 can be optionally configured such that the deformable member proximal end portion, as positioned during advancement within the body vessel or body cavity, stretches around the outer surface of the treatment device at the device distal end portion.

In Example 8, the system of any one or any combination of Examples 2-7 can be optionally configured such that the shaft proximal end portion includes a first locking mechanism portion and the device proximal end portion includes a second locking mechanism portion. The second locking mechanism portion can be configured to engage with the first locking mechanism portion.

In Example 9, the system of Example 8 can be optionally configured such that the first and second locking mechanism portions form a luer lock.

In Example 10, the system of any one or any combination of Examples 1-9 can be optionally configured such that the deformable member includes a hydrophilic coating or a hydrophobic, but lubricious, coating.

In Example 11, the system of any one or any combination of Examples 1-10 can be optionally configured such that the dilator assembly further includes a marker element detectable by imaging or electronic means. The marker element can be in the form of a marker band and can be disposed between the deformable member proximal end portion and the deformable member distal end portion.

In Example 12, the system of any one or any combination of Examples 1-11 can be optionally configured such that the dilator assembly is reusable.

In Example 13, the system of any one or any combination of Examples 1-12 can be optionally configured such that the tubular shaft includes a polyether ether ketone (PEEK), Nitinol, Ultem, or nylon material, or the deformable member includes an elastic material (e.g., polyether block amides, urethanes, styrene isoprene butadienes (SIBS), styrene ethylene butadienes (SEBS), or polyethylenes).

In Example 14, a system can comprise a dilator assembly and a treatment device. The dilator assembly can include a tubular shaft, extending from a shaft proximal end portion to a shaft distal end portion, and a deformable member. The deformable member can have an inner surface increasing in diameter between a deformable member distal end and a deformable member proximal end, wherein the distal and proximal ends are described in terms of their positioning during advancement of the system within a body vessel or body cavity. The deformable member distal end can be coupled to an outer surface of the tubular shaft, at or near the shaft distal end portion. The treatment device can extend a length less than a length of the tubular shaft, from a device proximal end to a device distal end, and can have a lumen diameter greater than a largest diameter of the outer surface of the tubular shaft. As a result, the tubular shaft and the deformable member can be removed, from the device proximal end, through the treatment device lumen when the proximal end portion of the deformable member is folded back around the shaft distal end portion.

In Example 15, a method can comprise sheathless introduction of a treatment device into a body vessel or body cavity, including inserting the treatment device coupled with a dilator assembly into the body vessel or body cavity; advancing the treatment device and the dilator assembly to a target location within the body vessel or body cavity; after reaching the target location within the body vessel or body cavity, decoupling the treatment device from the dilator assembly, including decoupling a distal end portion of the treatment device from a proximal end portion of a deformable member; and removing the dilator assembly from the treatment device, including fully retracting a tubular shaft and the deformable member through a lumen of the treatment device.

In Example 16, the method of Example 15 can optionally further comprise coupling the treatment device and the dilator assembly, including advancing the distal end portion of the treatment device into the proximal end portion of the deformable member.

In Example 17, the method of Example 16 can optionally further comprise, prior to coupling the treatment device and the dilator assembly, inverting the proximal end portion of the deformable member from a distal-facing orientation to a proximal-facing orientation to receive the distal end of the treatment device.

In Example 18, the method of any one or any combination of Examples 15-17 can optionally further comprise coupling the treatment device and the dilator assembly, including configuring a distal end portion of the tubular shaft to protrude beyond the distal end portion of the treatment device during advancement of the treatment device and the dilator assembly to the target location.

In Example 19, the method of any one or any combination of Examples 15-18 can optionally be configured such that inserting the treatment device coupled with the dilatory assembly into the body vessel or body cavity includes introducing a treatment device, having an outer diameter greater than a natural body vessel or body cavity diameter, into the body vessel or body cavity such that the proximal end portion of the deformable member is positioned between an outer surface of the distal end portion of the treatment device and an inner surface of the body vessel or body cavity.

In Example 20, the method of any one or any combination of Examples 15-19 can optionally be configured such that inserting the treatment device coupled with the dilator assembly into the body vessel or body cavity includes introducing a treatment device, having an outer diameter equal to or greater than about 6-Fr, into a radial artery such that the proximal end portion of the deformable member is positioned between an outer surface of the distal end portion of the treatment device and an inner surface of the radial artery.

In Example 21, the method of any one or any combination of Examples 15-20 can optionally be configured such that advancing the treatment device and the dilator assembly to the target location includes increasing an intersection of the proximal end portion of the deformable member over an outer surface of the distal end portion of the treatment device.

In Example 22, the method of any one or any combination of Examples 15-21 can optionally further comprise identifying the target location of the treatment device and the dilator assembly within the body vessel or body cavity, including using a marker element associated with the dilator assembly.

In Example 23, the method of any one or any combination of Examples 15-22 can optionally be configured such that decoupling the treatment device from the dilator assembly includes pushing a proximal end portion of the tubular shaft forward to detach and space the proximal end portion of the deformable member from the distal end portion of the treatment device.

In Example 24, the method of Example 23 can optionally be configured such that removing the dilator assembly from the treatment device includes using the spacing between the proximal end portion of the deformable member and the distal end portion of the treatment device to provide a period of force-reduced pulling of the tubular shaft from its proximal end portion.

In Example 25, the method of any one or any combination of Examples 15-24 can optionally be configured such that decoupling the treatment device from the dilator assembly includes disengaging a first locking mechanism portion associated with a proximal end portion of the dilator assembly and a second locking mechanism portion associated with a proximal end portion of the treatment device.

In Example 26, the method of any one or any combination of Examples 15-25 can optionally be configured such that retracting the tubular shaft and the deformable member through the lumen of the treatment device includes causing the proximal end portion of the deformable member to fold back towards a reduced-diameter portion of the tubular shaft.

In Example 27, the method of Example 26 can optionally be configured such that causing the proximal end portion of the deformable member to fold back toward the reduced-diameter portion of the tubular shaft includes causing the proximal end portion or an intermediate portion of the deformable member to be positioned proximal of a distal end portion of the deformable member, which is coupled to an outer surface of the tubular shaft.

In Example 28, the method of Example 26 can optionally be configured such that causing the proximal end portion of the deformable member to fold back toward the reduced-diameter portion of the tubular shaft includes causing the proximal end portion and an intermediate portion of the deformable member to be positioned distal of a distal end portion of the deformable member, which is coupled to an outer surface of the tubular shaft.

In Example 29, the method of any one or any combination of Examples 15-28 can optionally further comprise overturning the deformable member, relative to the tubular shaft, for reuse.

In Example 30, the vascular dilator system or method of any one or any combination of Examples 1-29 can optionally be configured such that all elements or options recited are available to use or select from.

These and other examples and features of the present vascular dilator systems, kits, and methods will be set forth in part in the following Detailed Description. This Overview is intended to provide non-limiting examples of the present subject matter—it is not intended to provide an exclusive or exhaustive explanation of the invention. The Detailed Description below is included to provide further information about the present vascular dilator systems, kits, and methods.

BRIEF DESCRIPTION OF THE DRAWINGS

In the drawings, like numerals can be used to describe similar elements throughout the several views. Like numerals having different letter suffixes can be used to represent different views or the progression of use of similar elements. The drawings illustrate generally, by way of example, but not by way of limitation, various embodiments discussed in the present document.

FIG. 2A illustrates a first step of a minimally invasive technique for accessing a body vessel or body cavity using a hollow needle.

FIG. 2B illustrates a second step of the minimally invasive technique for accessing a body vessel or body cavity using the hollow needle and a guide wire.

FIG. 2C illustrates a third step of the minimally invasive technique for accessing a body vessel or body cavity, including removal of the hollow needle.

FIG. 2D illustrates a fourth step of the minimally invasive technique for accessing a body vessel or body cavity, including advancing a treatment device over the guide wire.

DETAILED DESCRIPTION

The present inventors recognize, among other things, a need for gaining access into a body vessel or body cavity of a patient, such as a radial or femoral artery, while protecting vessel or cavity walls and preserving vessel or cavity access size (e.g., effective vessel diameter or cross-sectional area). Using this larger-than-conventional access size, caregiver-selected treatment devices can be efficiently introduced into a desired body vessel or body cavity during a minimally invasive procedure.

The present vascular dilator systems, kits, and methods comprise or use a dilator assembly including a tubular shaft and a deformable member. Together, the tubular shaft and the deformable member can allow for sheathless introduction of a treatment device into a body vessel or body cavity in a safer and less painful manner than is currently possible. The tubular shaft can have an outer surface that gradually increases in diameter between a shaft distal end portion and a shaft proximal end portion, thereby gradually expanding an inner diameter of a body vessel, for example, as the dilator assembly is introduced and advanced within a patient. The deformable member can be coupled to the outer surface of the tubular shaft, such as at or near the shaft distal end portion, and can provide a smooth, edge free surface to inhibit tearing or damage of the vessel wall as the treatment device is advanced within the patient.

In the absence of the deformable member being placed between an outer surface of the treatment device and an inner wall surface of the body vessel, the vessel wall may be damaged, a patient may experience pain or discomfort as the treatment device is being introduced into the vessel (e.g., due to an open distal end edge of the treatment device catching on vessel wall tissue), and/or the vessel may involuntarily spasm, preventing internal advancement of the treatment device.

By design, a proximal end portion of the deformable member can be sized to receive or stretch over and surround a distally-located outer surface portion of the treatment device during insertion. Post-insertion, the deformable member and the tubular shaft can be removed through a lumen of the treatment device by pulling on a proximal end portion of the tubular shaft. As the tubular shaft is pulled rearwards, from the shaft proximal end portion, the proximal end portion of the deformable member can be caused to deform and fold back towards the reduced-diameter of a shaft distal end portion (i.e., the proximal end portion of the deformable member can invert). The inverting of the proximal end portion of the deformable member onto the reduced-diameter portion of the tubular shaft allows the deformable member and the tubular shaft to fit through the lumen of the treatment device.

Figure 1:
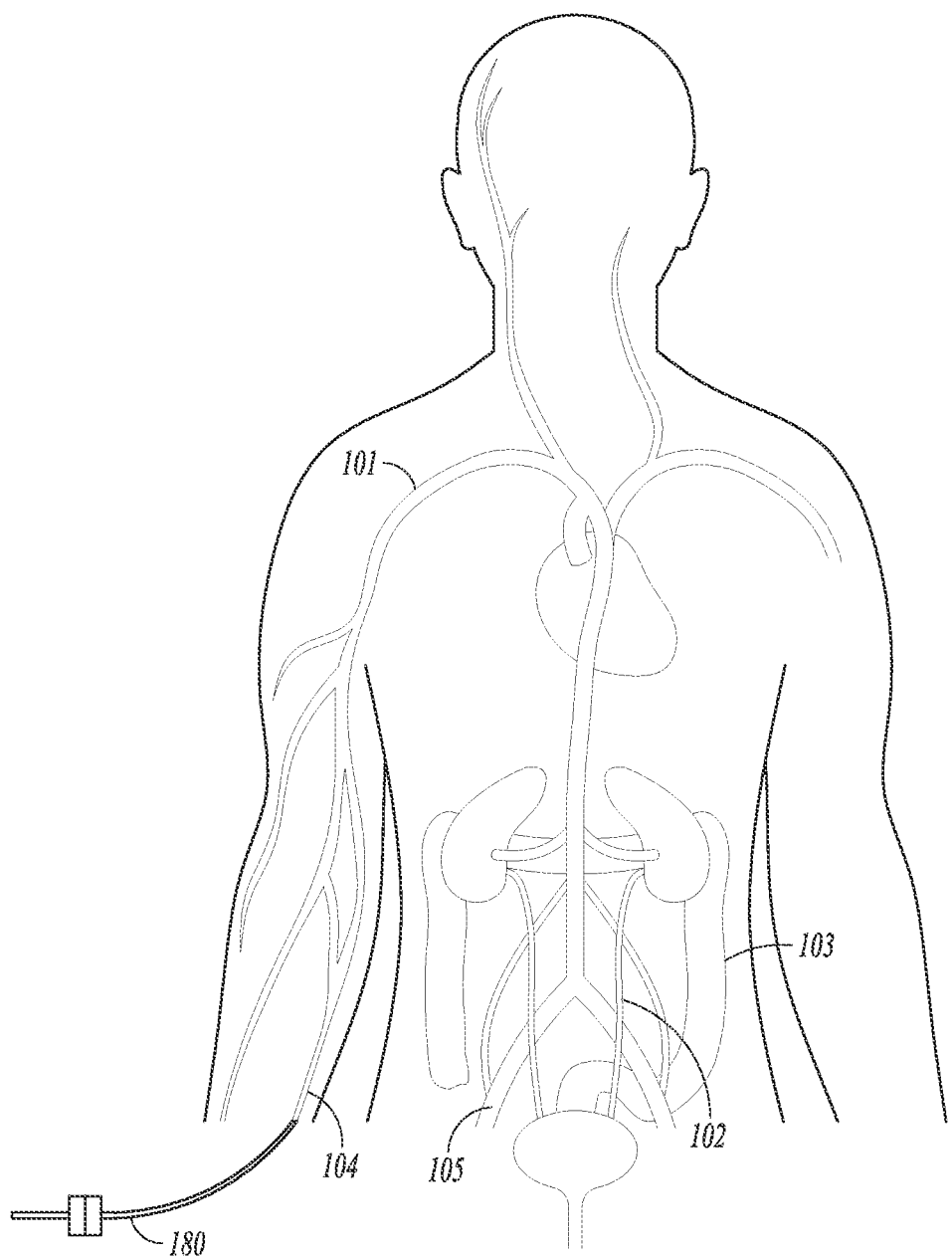
FIG. 1 illustrates vascular structures, urinary tract structures, and digestive tract structures in which vascular dilator systems, kits, and methods, as constructed in accordance with various embodiments, can be used.

FIG. 1 illustrates vascular structures 101 (e.g., radial and femoral arteries), urinary tract structures 102, and digestive tract structures 103, which provide suitable environments for using the present vascular dilator systems 180, kits, and methods. A radial artery 104 is located in a patient's forearm and, for a typical adult, has a natural inner diameter sufficient to allow percutaneous placement of a tubular introducer sheath or a treatment device having a size of up to 6-Fr. A femoral artery 105 is partially located in a patient's groin area and, for a typical adult, has a natural inner diameter sufficient to allow percutaneous placement of a tubular introducer sheath or a treatment device having a size of up to 9-Fr. The present vascular dilator systems 180, kits, and methods can be guided within the vascular 101, urinary tract 102, and digestive tract structures 103 using minimally invasive access techniques, such as the Seldinger technique.

FIGS. 2A-2D illustrate steps of the Seldinger technique for accessing a body vessel 241, for example. At FIG. 2A, a small access hole can be initiated by piercing a patient's skin 290, a wall of the body vessel 241, and any intermediate structures using a hollow needle 201. With the hollow needle 201 in place, a guide wire 230 can be advanced within an inner lumen of the needle 201 and into the body vessel 241, as illustrated in FIG. 2B. The guide wire can provide a railway into the body vessel 241. As illustrated in FIG. 2C, the hollow needle 201 can be removed, such as by sliding it off a proximal end of the guide wire 230, and the guide wire 230 can be further advanced within the body vessel 241 until it reaches a desired location. As illustrated in FIG. 2D, a treatment device 210 (e.g., a guide catheter) can be advanced over the guide wire and into the body vessel for use in a diagnostic, therapeutic, or other procedure. Advancement of the treatment device 210 into the body vessel can include the use of a tubular introducer sheath or a sheathless introducer system.

In certain circumstances, it can be advantageous to perform a minimally invasive procedure through a radial artery 104 (FIG. 1) rather than a larger, femoral artery 105 (FIG. 1). For example, vascular access through the radial artery 104 can help to reduce recovery time. However, typical minimally invasive procedures performed using a conventional thick, fixed-diameter tubular introducer sheath cannot be achieved through the smaller radial artery 104, because the sheath itself occupies too much of the valuable cross-sectional access space afforded by the radial artery 104. Conventional sheathless vascular introducer systems seek to solve this problem and provide the advantage of not losing part of a vessel's cross-section to a sheath. However, such sheathless systems suffer from the lack of any vessel protection during a minimally invasive procedure, such as during the introduction of a treatment device.

Figure 3A:
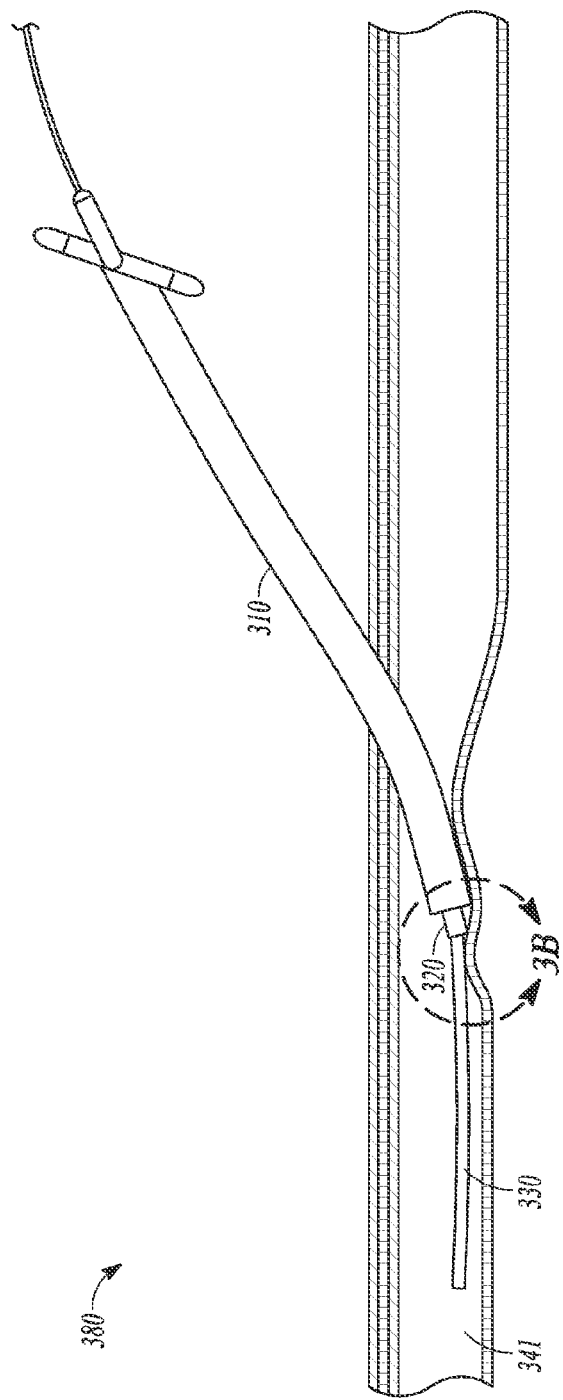
FIG. 3A illustrates an existing system for introducing a treatment device into a body vessel, in which a distal end of the treatment device is exposed.
Figure 3B:
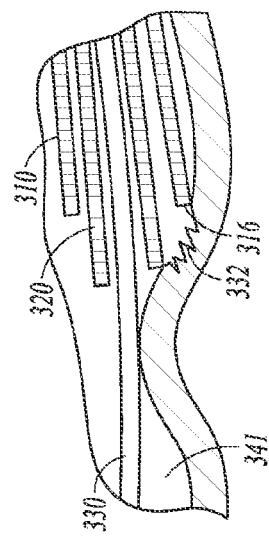
FIG. 3B illustrates a close up view of a portion of an existing system for introducing a treatment device into a body vessel, such as the system illustrated in FIG. 3A, in which a distal end of the treatment device can catch an opening or irregularity in a vessel wall causing vessel deformation or damage and patient pain.

FIGS. 3A and 3B illustrate an example of an existing sheathless system 380 for introducing a treatment device 310 into a body vessel 341 using a guide wire 330. The guide wire 330 can be placed by the Seldinger technique. The existing sheathless system 380 can include a tubular shaft 320, positionable within a lumen of the treatment device 310, configured to ride the guide wire 330 rail within the body vessel 341. As illustrated in FIG. 3B, the existing sheathless system 380 fails to provide a suitable means to prevent an open distal end edge 316 of the treatment device 310 from catching (or "fish mouthing" on) an opening 332 or other irregularity of a vessel wall as the tubular shaft 320 is advanced along the guide wire 330 rail. Any time a distal end portion of the existing sheathless system 380 is inserted within a patient or is advanced at a non-parallel angle relative to an adjacent vessel or cavity wall, such as during initial insertion or while moving around a bend, the distal end edge of the treatment device 310 can be prone to catching on and damaging bodily tissue or rolling back on itself and causing tissue damage due to its overlapped size.

In an attempt to prevent catching of the distal end edge 316 of the treatment device 310 on bodily tissue, other existing sheathless systems include a tubular shaft having a distal end portion diametrically-sized greater than a distal end portion of a treatment device. The enlarged distal end portion of the tubular shaft is intended to expand an inner diameter of a natural body vessel, for example, over a distal end portion of the treatment device. However, the enlarged distal end portion makes it difficult to remove the tubular shaft after the treatment device has reached a desired location within the body vessel and further, the enlarged portion may tear a wall of the body vessel as it is advanced within a patient.

A technological concept of the present vascular dilator systems, kits, and methods is to provide or use a sheathless configuration for introducing a treatment device within a body vessel or body cavity, while protecting bodily tissue during insertion, and having components that are easily removed after the treatment device reaches a desired location within the body vessel or body cavity. The sheathless configuration can allow for the introduction of treatment devices having an outer surface diameter approximately equal to, or in some cases greater than, the natural inner diameter of the body vessel or body cavity. For example, the sheathless configuration can allow for the introduction of treatment devices having an outer surface diameter approximately equal to or greater than 4-French (Fr), 5-Fr, or 6-Fr for radial arteries 104 (FIG. 1) and approximately equal to or greater than 6-Fr, 7-Fr, 8-Fr, or 9-Fr for femoral arteries 105. Various examples of the present vascular dilator systems, kits, and methods are illustrated in FIGS. 4-9. The vascular dilator systems 480, 580, 680, 780, 880 and kits are available in various sizes, such as 4-Fr, 5-Fr, 6-Fr, 7-Fr, 8-Fr, and 9-Fr and can include a dilatory assembly and, optionally, a treatment device or a portion of a treatment device. Similar configurations of the vascular dilator systems, kits, and methods can be used for its various size offerings.

Figure 4:
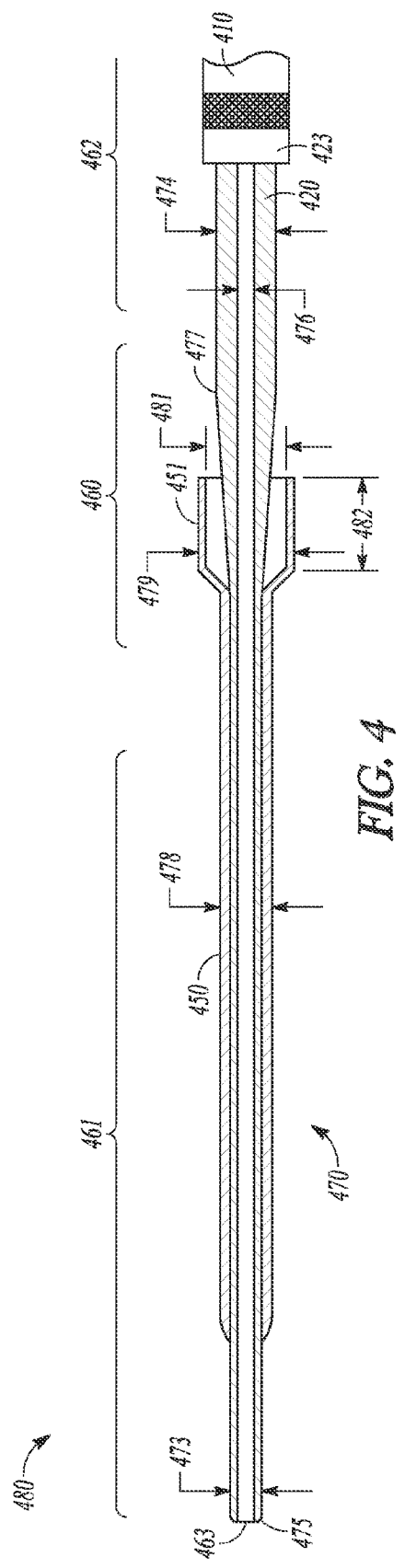
FIG. 4 illustrates a distal end portion of a treatment device partially advanced onto a dilator assembly, which is shown in cross-section, as constructed in accordance with at least one embodiment.

FIG. 4 illustrates a distal end portion of a treatment device 410 partially advanced onto a dilator assembly 470, the latter of which is shown in cross-section and according to one embodiment. The dilator assembly 470 can include a tubular shaft 420 and a deformable member 450.

The tubular shaft 420 can be made of a PEEK, Nitinol, Ultem, or nylon material and can include a relatively narrow distal end portion 461, a tapered intermediate portion 460, and a proximal end portion 462 having a diameter less than the treatment device 410. The distal end portion 461 of the tubular shaft 420 can include an outer surface diameter 473 of about 0.02 inches to about 0.04 inches, inclusive, such as about 0.027 inches. The proximal end portion 462 of the tubular shaft can include an outer surface diameter that can slide inside a lumen of the treatment device 410. In an example, the proximal end portion 462 can include an outer surface diameter 474 of about 0.030 inches to about 0.80 inches, inclusive, such as about 0.074 inches. The intermediate portion 460 can include a taper 477 of about 5 degrees to about 45 degrees, inclusive, which provides a transition from the relatively narrow distal end portion 461 to the proximal end portion 462.

The tubular shaft 420 can be configured with sufficient flexibility to be advanced into body vessels or body cavities and navigate bends as its inner lumen, having a diameter about 0.010 inches to about 0.040 inches (e.g., 0.020 inches), follows a guide wire rail. A tip 463 of the tubular shaft 420 can be atraumatically configured to aid in the advancement along the guide wire rail through curves or bends in a body vessel or body cavity. The tip 463 can include a radius 475 of about 0.008 inches to about 0.080 inches, such as about 0.016 inches.

A distal end or distal end portion of the deformable member 450 can be coupled to an outer surface of the distal end portion 461 of the tubular shaft 420. In the example illustrated, the distal end portion of the deformable member 450 can include an inner surface diameter that closely fits a reduced outer surface diameter 473 at the distal end portion 461 of the tubular shaft 420. As shown, the deformable member 450 can be positioned such that its proximal end portion initially has a proximal-facing orientation to receive a distal end band portion 423 of the treatment device 410. Optionally, the deformable member 450 can be positioned such that its proximal end portion initially has a distal-facing orientation and has to be inverted onto itself to receive the distal end band portion 423 of the treatment device 410. When the proximal end portion is oriented to receive the distal end band portion 423, the tubular shaft 420 protrudes from the deformable member's proximal and distal end portions.

In both orientations, the proximal end portion of the deformable member 450 can include a larger inner surface diameter than the diameter of the distal end portion. The distal end portion of the deformable member 450 can include an outer surface diameter 478 of about 0.03 inches to about 0.08 inches, inclusive, such as 0.056 inches. The proximal end portion of the deformable member 450 can at least partially expand over the tapered intermediate portion 460 of the tubular shaft 420, such that sufficient space is present between its inner surface diameter 481 and the outer surface diameter of the adjacent tubular shaft 420 portion. The space can create a flap 451 configured to receive or stretch around a distal end band portion 423 of the treatment device 410. The flap 451 can prevent a distal end edge of the treatment device 410 from catching on an opening, irregularity, or bend in the body vessel or body cavity or on a wall of the body vessel or body cavity. The flap 451 can include a length 482 of about 0.050 inches to about 0.250 inches, inclusive, such as about 0.125 inches. The proximal end portion of the deformable member 450 can include an outer surface diameter 479 of about 0.03 inches to about 0.80 inches, inclusive, such as about 0.094 inches and an inner surface diameter 481 of about 0.03 inches to about 0.77 inches, inclusive, such as about 0.084 inches.

The deformable member 450 can be made of a non-biodegradable and elastic material, such as polyether block amides, urethanes, styrene isoprene butadienes (SIBS), styrene ethylene butadienes (SEBS), or polyethylenes, and can include a hydrophilic coating or a hydrophobic, but lubricious, coating to facilitate advancement within a patient. The hydrophilic coating or hydrophobic, but lubricious, coating can be wholly or partly applied to an outer and/or inner surface of the deformable member 450. It has been found that similar functionality can be achieved with hydrophilic coatings and with lubricious hydrophobic coatings. In some examples, lubricious hydrophobic coatings can be a cost effective alternative to hydrophilic coatings. Non-biodegradable deformable members 450 can provide internal use that is not dependent on a degradation time period. This flexibility can be advantageous for many present and future medical procedures and removes potentially dangerous unknowns, including premature degradation.

Figure 5:
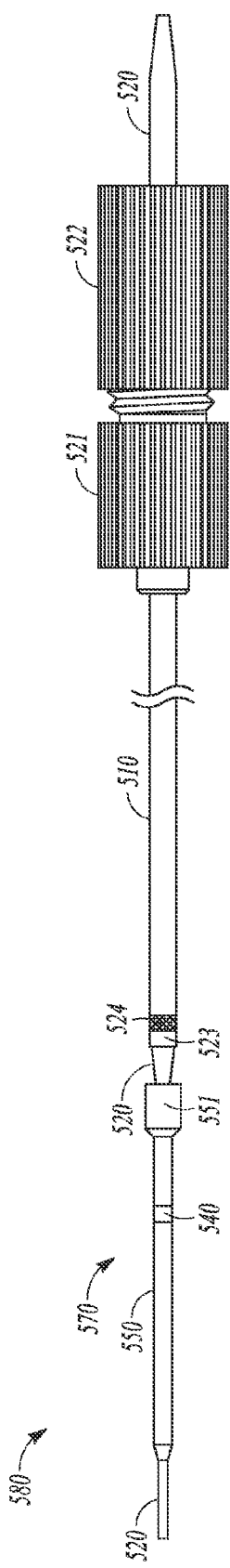
FIG. 5 illustrates a schematic view of a treatment device mostly advanced onto a dilator assembly, as constructed in accordance with at least one embodiment.

FIG. 5 illustrates a schematic view of a treatment device 510 mostly advanced onto a dilator assembly 570, including a tubular shaft 520 and a deformable member 550. Proximal end portions of the tubular shaft 520 and the treatment device 510 can include locking mechanism portions. For example, a first locking mechanism portion 521 can be disposed at the proximal end portion of the treatment device 510 and a second locking mechanism portion 522 can be disposed near the proximal end portion of the tubular shaft 520. The first and second locking mechanism portions 521, 522 can lock the tubular shaft 520 and the treatment device 510 as the system 580 is advanced into a body vessel or body vessel. In an example, the locking mechanism portions 521, 522 form a luer lock. As the locking mechanism portions 521, 522 converge toward one another, but before engagement, a distal end band portion 523 of the treatment device 510 can advance (e.g., slide) into a flap 551 at a proximal end portion of the deformable member 550. When the distal end band portion 523 is positioned in the flap 551 as desired, the locking mechanism portions 521, 522 can be engaged, thereby preventing relative movement between the treatment device 510 and the dilator assembly 570. As illustrated, the tubular shaft 520 can extend a length greater than a length of the treatment device 510 such that when the locking mechanism portions 521, 522 are fully engaged, portions of the tubular shaft 520 protrude at proximal and distal ends of the system 580. In an example, the length of the tubular shaft 520 is about 130 centimeters.

One or both of a locator band 524, positioned near the distal end of the treatment device 510, or a marker band 540, positioned on the deformable member 550, can be used by a caregiver to locate the system 580 as it travels through a body vessel or body cavity. In an example, the marker band 540 can be crimped around an intermediate portion of the deformable member 550 and can include a material that can be detected by imaging or electronic means.

Figure 6:
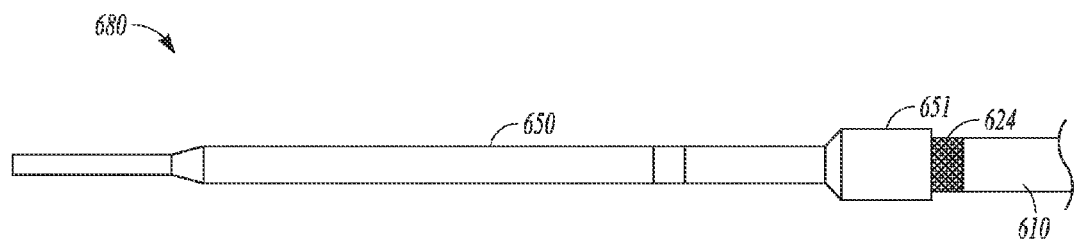
FIG. 6 illustrates a schematic view of a distal end portion of a treatment device positioned within a proximal end portion of a deformable member, such as when a proximal end portion of a tubular shaft and a proximal end portion of the treatment device are fully engaged, as constructed in accordance with at least one embodiment.

FIG. 6 illustrates a distal end portion of a treatment device 610 positioned within a flap 651 at a proximal end portion of a deformable member 650, such as when proximally-located locking mechanism portions of the treatment device 610 and a tubular shaft are fully engaged with one another. The distal end band 523 of the treatment device, as illustrated in FIG. 5, can no longer be seen, while a locator band 624 is positioned adjacent the proximal end portion of the deformable member 650.

Figure 7:
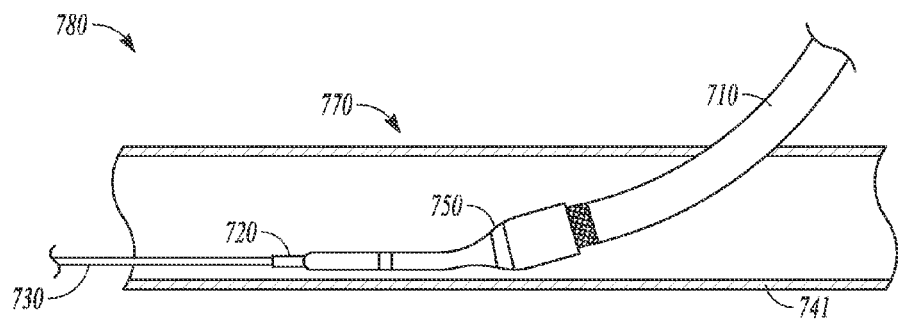
FIG. 7 illustrates an example of a system for introducing a treatment device into a body vessel, in which a distal end portion of the treatment device is surrounded by a proximal end portion of a deformable member, thereby protecting a body vessel wall during insertion.

FIG. 7 illustrates how a present vascular dilator system 780, including a dilator assembly 770 and, optionally, a treatment device 710 can be deployed into a body vessel 741 or body cavity. A tubular shaft 720 of the dilator assembly 770 can guide the treatment device 710 over a guide wire rail 730, while a deformable member 750 of the dilator assembly 770 can provide a smooth, edge free surface to inhibit tearing or damage of a body vessel wall, for example, as the treatment device 710 is internally advanced within a patient. As discussed above in relation to FIG. 5, locking mechanism portions of the treatment device 710 and the tubular shaft 720 can prevent relative movement between the elements during advancement within the patient. If the deformable member 750 deforms during advancement, such deformation advantageously results in further coverage, and prevents roll-up, of a distal end of the treatment device 710.

After the vascular dilator system has been pushed along the guide wire 730 to a target location within the body vessel 741, for example, the tubular shaft 720 can be pulled rearwards from its proximal end portion, after disengaging the locking mechanism portions, as the treatment device is held in place. The pulling of the tubular shaft 720 can cause the proximal end portion of the deformable member 750 to deform and fold back towards the reduced-diameter of a distal end portion of the tubular shaft 720 (i.e., the proximal end portion of the deformable member can invert) and the dilator assembly 770 can be removed through an inner lumen of the treatment device 710. A dilator assembly 770 that is completely removable through a treatment device lumen can provide a quick and safe removal method in body vessels and body cavities where a risk of blockage or foreign matter can be highly dangerous. Thus, not only does the present vascular dilator system 780 provide a sheathless configuration, allowing for the safe introduction of various sized treatment devices into body vessels and body cavities, but the system 780 is designed so that its components are easily removed after a treatment device reaches a desired location within the body vessel or body cavity.

Figure 8A:
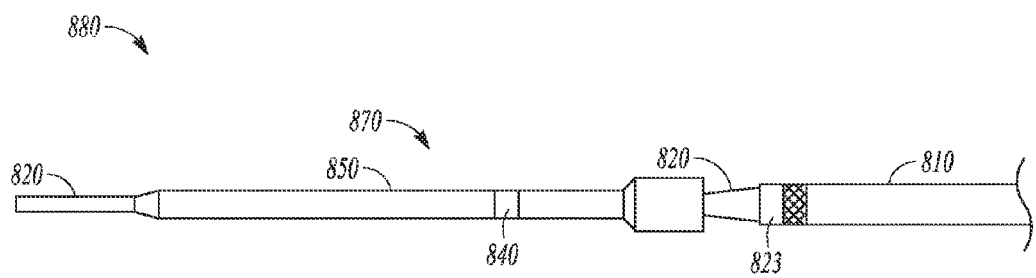
FIGS. 8A and 8B illustrate distal end portions of a treatment device and a dilator assembly, at successive stages as the dilator assembly is being withdrawn through an inner lumen of the treatment device.
Figure 8B:
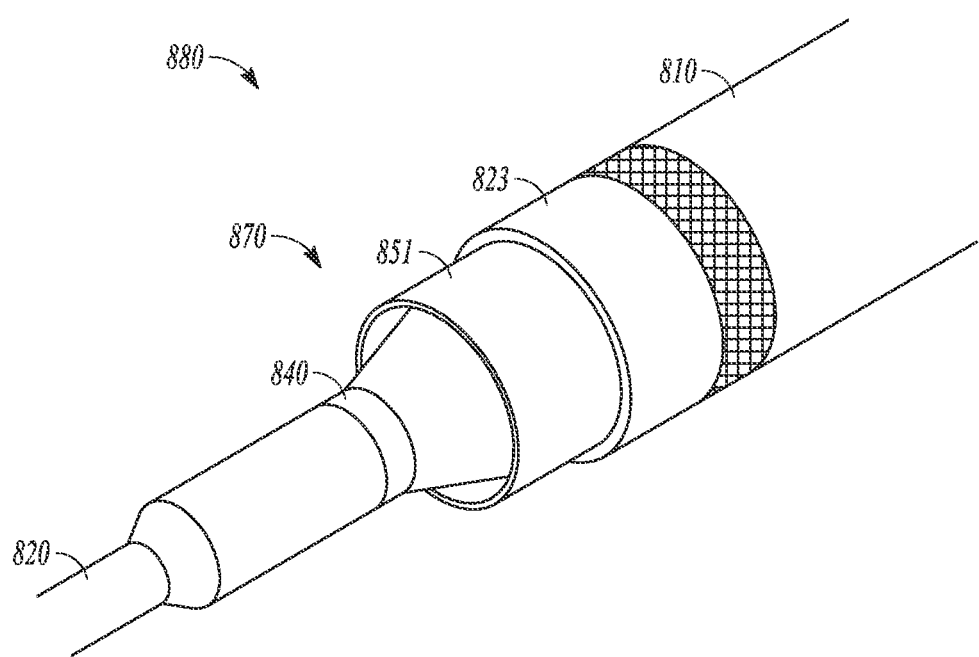

FIGS. 8A and 8B illustrate distal end portions of a treatment device 810 and a dilator assembly 870, including a tubular shaft 820 and a deformable member 850, at successive stages as the dilator assembly 870 is being withdrawn through an inner lumen of the treatment device 810. As illustrated in FIG. 8A, the dilator assembly 870 can initially be pushed forward a small distance, from a proximal end portion of the tubular shaft 820, so that a proximal end portion of the deformable member 850 can become disengaged and spaced from a distal end band portion 823 of the treatment device 810. Alternatively, the dilator assembly 870 can be retracted by pulling on the proximal end portion of the tubular shaft 820 and the proximal end portion of the deformable member 850 will subsequently be pulled from the distal end band portion 823 of the treatment device 810. Pulling on the proximal end portion of the tubular shaft 820 can cause a marker band 840, positioned on the deformable member 850, to retract towards a proximal end of the treatment device 810. Pulling on the proximal end portion of the tubular shaft 820 can also cause a flap 851 at the proximal end portion of the deformable member 850 to invert towards the distal end portion of the tubular shaft 820, as illustrated in FIG. 8B. Once inverted, the distal end portion of the tubular shaft 820 and the deformable member 850 can fit through the lumen of the treatment device 810, and the dilator assembly 870 can be removed from the body vessel or body cavity.

A kit can include a hollow needle, a guide wire, a vascular dilator system 480, 580, 680, 780, 880 including a dilator assembly and, optionally, a treatment device or a portion of the treatment device, and instructions for using the vascular dilator system to insert the treatment device into a body vessel or body cavity. In some examples, the instructions can provide guidance for inserting a treatment device or a portion of a treatment device into a radial artery 104 (FIG. 1) or a femoral artery 105 (FIG. 1).

Figure 9:
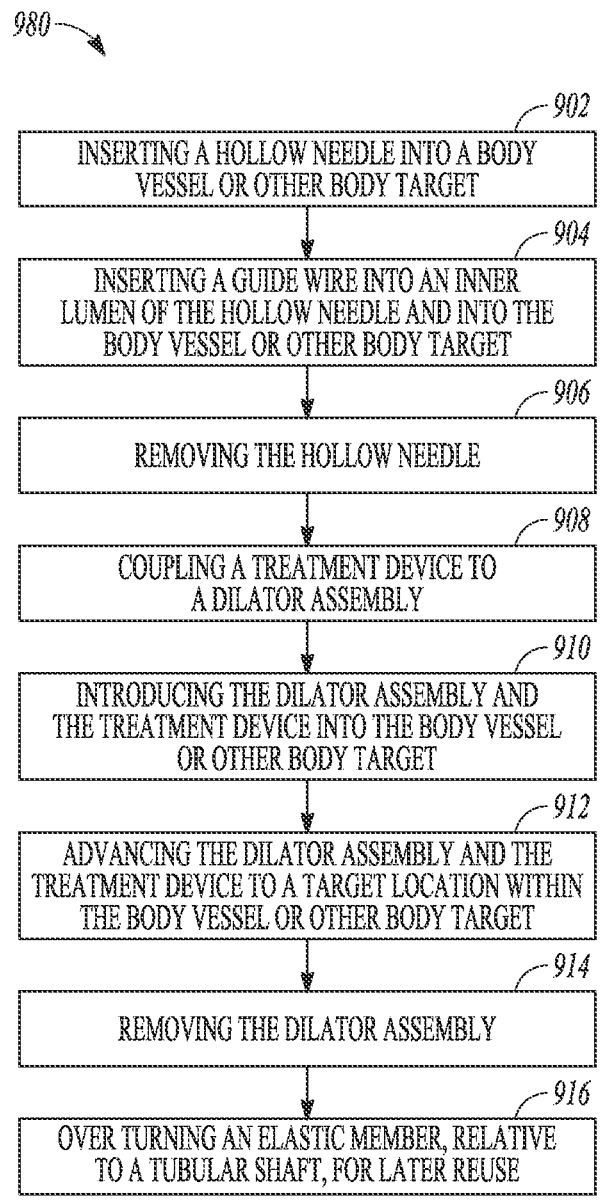
FIG. 9 illustrates an example method of using a vascular dilator system or kit, as constructed in accordance with at least one embodiment.

FIG. 9 illustrates an example method 980 of using a vascular dilator system or kit including a hollow needle, a guide wire, a dilator assembly and, optionally, a treatment device, as conceived by the present inventors. The treatment device can be implanted by first inserting the hollow needle into a body vessel in operation 902. As an alternative to a body vessel, the target can be a hollow body organ, solid tissue location, body cavity, or the like. The guide wire can then be inserted through an inner lumen of the hollow needle, in operation 904, and into the body vessel, thereby providing a railway to the body vessel. Once the guide wire is in place, the hollow needle can be removed in operation 906.

The treatment device can be coupled to the dilator assembly in operation 908. A distal end portion of the treatment device can be inserted into a proximal end portion of a deformable member, of the dilator assembly, and a proximal end portion of the treatment device can be engaged with a proximal end portion of a tubular shaft, of the dilator assembly. In an example, a locking mechanism portion associated with the treatment device is engaged with a locking mechanism portion associated with the tubular shaft. In an example, the proximal end portion of the deformable member can be inverted from a distal-facing orientation to a proximal-facing orientation prior to receiving the distal end portion of the treatment device.

In operation 910, the dilator assembly and the treatment device can be introduced into the body vessel using an over-the-guide wire technique, with the guide wire passing through an inner lumen of the tubular shaft. The tubular shaft can include an atraumatic distal end portion that leads the way into the body vessel. The dilator assembly and the treatment device can be advanced to a target location within the body vessel, in operation 912. A caregiver can guide the dilator assembly and the treatment device to the target location using one or both of a locator band, positioned near the distal end of the treatment device, or a marker band, positioned on the deformable member, and imaging or electronic means. Advancement of the dilator assembly can cause the deformable member to deform and result in further coverage of the distal end portion of the treatment device.

After reaching the target location within the body vessel, the dilator assembly can be removed in operation 914. Removal of the dilator assembly can include disengaging a first locking mechanism portion associated with the proximal end portion of the tubular shaft and a second locking mechanism portion associated with the proximal end portion of the treatment device. After the locking mechanism portions are disengaged, removal of the dilator assembly can optionally include pushing the tubular shaft, from a proximal end portion, about 1 centimeter to about 3 centimeters, inclusive, to uncover the distal end of the treatment device and then pulling on the proximal end portion of the tubular shaft while maintaining a position of the treatment device. This can cause a decoupling between the distal end portion of the treatment device and the proximal end portion of the deformable member (if not already decoupled), the inversion of the proximal end portion of the deformable member towards the distal end portion of the tubular shaft, and the full retraction of the tubular shaft and the deformable member through a lumen of the treatment device.

The inversion of the proximal end portion of the deformable member can vary depending on its orientation when the distal end portion of the deformable member is coupled to the tubular shaft. If, for example, the deformable member is positioned such that its proximal end portion initially has a proximal-facing orientation to receive the distal end portion of the treatment device, the inversion of the proximal end portion can include positioning the proximal end portion or an intermediate portion of the deformable member proximal of the distal end portion of the deformable member. If, for example, the deformable member is positioned such that its proximal end portion initially has a distal-facing orientation and has to be inverted onto itself to receive the distal end portion of the treatment device, the inversion of the proximal end portion can include positioning the proximal end portion and the intermediate portion of the deformable member distal of the distal end portion of the deformable member. The orientation of the proximal end portion of the deformable member, when its distal end portion is coupled to the tubular shaft, can also determine whether one or two layers of the deformable member are positioned (on a per side basis) between the outer surface of the tubular shaft and lumen walls of the treatment device during removal. If the deformable member's proximal end portion has a proximal-facing orientation, two layers of the deformable member (per side) exist between the outer surface of the tubular shaft and lumen walls of the treatment device. If the deformable member's proximal end portion has a distal-facing orientation, one layer of the deformable member (per side) exists between the outer surface of the tubular shaft and the lumen walls of the treatment device, thereby providing greater removal spacing.

In operation 916, the inverted elastic member can optionally be overturned, relative to the tubular shaft, for later reuse.

Closing Notes:

Body vessel and body cavity cross-sectional access size constitutes one of the principal limitations of minimally invasive medical procedures. The present vascular dilator systems, kits, and methods can include or use a dilator assembly, including a tubular shaft and a deformable member, and optionally, a treatment device or a portion of a treatment device. Advantageously, the tubular shaft and the deformable member enable the treatment device to be inserted into a body vessel or body cavity of interest (e.g., a radial artery) without using a tubular introducer sheath and without causing harm to bodily tissue (e.g., a vessel wall, cavity wall, or tissue along an insertion track outside of the vessel or cavity and under the skin surface). Additionally, the deformable member can provide a tapered bridge between an outer surface of the tubular shaft and an outer surface of the treatment device. The tapered bridge can gradually stretch the natural inner diameter of the body vessel or body cavity of interest allowing treatment devices having an outer surface diameter approximately equal to or greater than the natural inner diameter to be used.

A proximal end of the deformable member can include a larger inner surface diameter than a distal end, the latter of which can be secured to an outer surface of the tubular shaft. The outer surface of the tubular shaft can increase in diameter between a shaft distal end portion, to which the distal end of the deformable member is secured, and a shaft proximal end portion, thereby providing a gradual taper to the larger diameter of a treatment device. The larger inner surface diameter of the proximal end of the deformable member can be configured to receive or stretch around a distal end portion of the treatment device. During advancement within the body vessel or body cavity of interest, the deformable member bridges a gap between the outer surface of the tubular shaft and an outer surface of the treatment device. If the deformable member deforms during insertion, such deformation advantageously results in further coverage, and prevents roll-up, of the distal end of the treatment device.

When the treatment device is positioned as desired within the body vessel or body cavity of interest, the dilator assembly can be retracted by pulling on a proximal end portion of the tubular shaft. During retraction, the distal end portion of the dilator assembly is slid through a lumen of the treatment device and, in the process, a proximal end portion of the deformable member can be inverted onto the reduced-diameter of the shaft distal end portion. The inverting of the proximal end portion of the deformable member onto the reduced-diameter portion of the tubular shaft allows the deformable member and the tubular shaft to fit through the lumen of the treatment device. Advantageously, the deformable member can be everted, relative to the tubular shaft, and reused in a later procedure.

Among other things, it is believed that the dilator assembly, including the tubular shaft and the deformable member, can: (a) reduce axial stress on a body vessel or body cavity and associated pain or discomfort experienced by a patient, (b) inhibit involuntary vessel or cavity spasm, (c) protect body vessel and body cavity walls as a treatment device is introduced into a body vessel or body cavity, (d) without compromising vessel or cavity access size, and (e) be easily removed from a patient after the treatment device reaches a desired location within the body vessel or body cavity.

The above Detailed Description includes references to the accompanying drawings, which form a part of the Detailed Description. The drawings show, by way of illustration, specific embodiments in which the present vascular dilator systems, kits, and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the present vascular dilator systems, kits, and methods should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" are used to refer to an amount that is nearly, almost, or in the vicinity of being equal to a stated amount. In this document, the terms "proximal" and "distal" are used to refer to a system element location relative to a caregiver user. For example, a proximal element portion is a portion closer to the user of the system, whereas a distal element portion is a portion farther away from the user of the system, such as the portion interacting with a patient recipient. In this document, the term "patient" is meant to include mammals, such as for human applications or veterinary applications.

In the appended claims, the terms "including" and "in which" are used as the plain-English equivalents of the respective terms "comprising" and "wherein." Also, in the following claims, the terms "including" and "comprising" are open-ended, that is, a vascular dilator system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A method comprising:
   inverting a proximal end portion of a deformable member from a distal-facing orientation to a proximal-facing orientation to receive a distal end portion of a treatment device;
   coupling the treatment device and a dilator assembly comprising a tubular shaft and the deformable member, including advancing the distal end portion of the treatment device into the proximal end portion of the deformable member;
   sheathless introduction of the treatment device into a body vessel or body cavity, including inserting the treatment device coupled with the dilator assembly into the body vessel or body cavity;
   advancing the treatment device and the dilator assembly to a target location within the body vessel or body cavity;
   after reaching the target location within the body vessel or body cavity, decoupling the treatment device from the dilator assembly; and
   removing the dilator assembly from the treatment device, including fully retracting the tubular shaft and the deformable member through a lumen of the treatment device.

2. The method of claim 1, wherein coupling the treatment device and the dilator assembly includes coupling the treatment device and the dilator assembly such that a distal end portion of the tubular shaft protrudes beyond the distal end portion of the treatment device during advancement of the treatment device and the dilator assembly to the target location.

3. The method of claim 1, wherein the treatment device includes a natural outer diameter greater than a diameter of the body vessel or body cavity; and wherein inserting the treatment device coupled with the dilator assembly into the body vessel or body cavity includes introducing the treatment device into the body vessel or body cavity such that the proximal end portion of the deformable member is positioned between an outer surface of the distal end portion of the treatment device and an inner wall surface of the body vessel or body cavity.

4. The method of claim 1, wherein the treatment device includes an outer diameter equal to or greater than about 6-Fr; and wherein inserting the treatment device coupled with the dilator assembly into the body vessel or body cavity includes introducing the treatment device into a radial artery such that the proximal end portion of the deformable member is positioned between an outer surface of the distal end portion of the treatment device and an inner wall surface of the radial artery.

5. The method of claim 1, further comprising identifying the target location of the treatment device and the dilator assembly within the body vessel or body cavity, including using a marker element associated with the dilator assembly.

6. The method of claim 1, wherein decoupling the treatment device from the dilator assembly includes disengaging a first locking mechanism portion associated with a proximal end portion of the dilator assembly and a second locking mechanism portion associated with a proximal end portion of the treatment device.

7. A method comprising:
   sheathless introduction of a treatment device into a body vessel or body cavity, including inserting the treatment device coupled with a dilator assembly, comprising a tubular shaft and a deformable member, into the body vessel or body cavity;
   advancing the treatment device and the dilator assembly to a target location within the body vessel or body cavity, including increasing an intersection of a proximal end portion of the deformable member over an outer surface of a distal end portion of the treatment device;

after reaching the target location within the body vessel or body cavity, decoupling the treatment device from the dilator assembly; and removing the dilator assembly from the treatment device, including fully retracting the tubular shaft and the deformable member through a lumen of the treatment device.

8. The method of claim 7, further comprising, prior to sheathless introduction of the treatment device into the body vessel or body cavity, coupling the treatment device and the dilator assembly such that a distal end portion of the tubular shaft protrudes beyond the distal end portion of the treatment device during advancement of the treatment device and the dilator assembly to the target location.

9. The method of claim 7, wherein the treatment device includes a natural outer diameter greater than a diameter of the body vessel or body cavity; and wherein inserting the treatment device coupled with the dilator assembly into the body vessel or body cavity includes introducing the treatment device into the body vessel or body cavity such that the proximal end portion of the deformable member is positioned between an outer surface of the distal end portion of the treatment device and an inner wall surface of the body vessel or body cavity.

10. The method of claim 7, wherein the treatment device includes an outer diameter equal to or greater than about 6-Fr; and wherein inserting the treatment device coupled with the dilator assembly into the body vessel or body cavity includes introducing the treatment device into a radial artery such that the proximal end portion of the deformable member is positioned between an outer surface of the distal end portion of the treatment device and an inner wall surface of the radial artery.

11. The method of claim 7, further comprising identifying the target location of the treatment device and the dilator assembly within the body vessel or body cavity, including using a marker element associated with the dilator assembly.

12. The method of claim 7, wherein decoupling the treatment device from the dilator assembly includes disengaging a first locking mechanism portion associated with a proximal end portion of the dilator assembly and a second locking mechanism portion associated with a proximal end portion of the treatment device.

13. A method comprising:
sheathless introduction of a treatment device into a body vessel or body cavity, including inserting the treatment device coupled with a dilator assembly, comprising a tubular shaft and a deformable member, into the body vessel or body cavity;

advancing the treatment device and the dilator assembly to a target location within the body vessel or body cavity;

after reaching the target location within the body vessel or body cavity, decoupling the treatment device from the dilator assembly, including pushing a proximal end portion of the tubular shaft forward to detach and space a proximal end portion of the deformable member from a distal end portion of the treatment device; and removing the dilator assembly from the treatment device, including fully retracting the tubular shaft and the deformable member through a lumen of the treatment device.

14. The method of claim 13, wherein removing the dilator assembly from the treatment device includes using the spacing between the proximal end portion of the deformable member and the distal end portion of the treatment device to provide a period of force-reduced pulling of the tubular shaft from its proximal end portion.

15. The method of claim 13, further comprising, prior to sheathless introduction of the treatment device into the body vessel or body cavity, coupling the treatment device and the dilator assembly such that a distal end portion of the tubular shaft protrudes beyond the distal end portion of the treatment device during advancement of the treatment device and the dilator assembly to the target location.

16. The method of claim 13, wherein the treatment device includes a natural outer diameter greater than a diameter of the body vessel or body cavity; and wherein inserting the treatment device coupled with the dilator assembly into the body vessel or body cavity includes introducing the treatment device into the body vessel or body cavity such that the proximal end portion of the deformable member is positioned between an outer surface of the distal end portion of the treatment device and an inner wall surface of the body vessel or body cavity.

17. The method of claim 13, wherein the treatment device includes an outer diameter equal to or greater than about 6-Fr; and wherein inserting the treatment device coupled with the dilator assembly into the body vessel or body cavity includes introducing the treatment device into a radial artery such that the proximal end portion of the deformable member is positioned between an outer surface of the distal end portion of the treatment device and an inner wall surface of the radial artery.

18. The method of claim 13, further comprising identifying the target location of the treatment device and the dilator assembly within the body vessel or body cavity, including using a marker element associated with the dilator assembly.

19. The method of claim 13, wherein decoupling the treatment device from the dilator assembly includes disengaging a first locking mechanism portion associated with a proximal end portion of the dilator assembly and a second locking mechanism portion associated with a proximal end portion of the treatment device.

20. A method comprising:
sheathless introduction of a treatment device into a body vessel or body cavity, including inserting the treatment device coupled with a dilator assembly, comprising a tubular shaft and a deformable member, into the body vessel or body cavity;

advancing the treatment device and the dilator assembly to a target location within the body vessel or body cavity;

after reaching the target location within the body vessel or body cavity, decoupling the treatment device from the dilator assembly; and removing the dilator assembly from the treatment device, including fully retracting the tubular shaft and the deformable member through a lumen of the treatment device and causing a proximal end portion of the deformable member to fold back towards a reduced-diameter portion of the tubular shaft.

21. The method of claim 20, further comprising, prior to sheathless introduction of the treatment device into the body vessel or body cavity, coupling the treatment device and the dilator assembly such that a distal end portion of the tubular shaft protrudes beyond a distal end portion of the treatment device during advancement of the treatment device and the dilator assembly to the target location.

22. The method of claim 20, wherein the treatment device includes a natural outer diameter greater than a diameter of the body vessel or body cavity; and wherein inserting the treatment device coupled with the dilator assembly into the body vessel or body cavity includes introducing the treatment device into the body vessel or body cavity such that the proximal end portion of the deformable member is positioned between an outer surface of a distal end portion of the treatment device and an inner wall surface of the body vessel or body cavity.

23. The method of claim 20, wherein the treatment device includes an outer diameter equal to or greater than about 6-Fr; and wherein inserting the treatment device coupled with the dilator assembly into the body vessel or body cavity includes introducing the treatment device into a radial artery such that the proximal end portion of the deformable member is positioned between an outer surface of a distal end portion of the treatment device and an inner wall surface of the radial artery.

24. The method of claim 20, further comprising identifying the target location of the treatment device and the dilator assembly within the body vessel or body cavity, including using a marker element associated with the dilator assembly.

25. The method of claim 20, wherein decoupling the treatment device from the dilator assembly includes disengaging a first locking mechanism portion associated with a proximal end portion of the dilator assembly and a second locking mechanism portion associated with a proximal end portion of the treatment device.

26. The method of claim 20, wherein causing the proximal end portion of the deformable member to fold back toward the reduced-diameter portion of the tubular shaft includes causing the proximal end portion or an intermediate portion of the deformable member to be positioned proximal of a distal end portion of the deformable member, which is coupled to an outer surface of the tubular shaft.

27. The method of claim 20, wherein causing the proximal end portion of the deformable member to fold back toward the reduced-diameter portion of the tubular shaft includes causing the proximal end portion and an intermediate portion of the deformable member to be positioned distal of a distal end portion of the deformable member, which is coupled to an outer surface of the tubular shaft.

* * * * *